United States Patent [19]

Wong et al.

[11] Patent Number: 5,369,017
[45] Date of Patent: Nov. 29, 1994

[54] PROCESS FOR SOLID PHASE GLYCOPEPTIDE SYNTHESIS

[75] Inventors: Chi-Huey Wong, Rancho Sante Fe; Matthias Schuster, San Diego, both of Calif.

[73] Assignee: The Scripps Research Institute, La Jolla, Calif.

[21] Appl. No.: 191,777

[22] Filed: Feb. 4, 1994

[51] Int. Cl.⁵ .............................................. C12P 21/00
[52] U.S. Cl. .................................. 435/68.1; 435/175; 435/176; 435/193; 435/201
[58] Field of Search ................... 435/68.1, 193, 201, 435/175, 176

[56] References Cited

U.S. PATENT DOCUMENTS

| | | | |
|---|---|---|---|
| 4,315,074 | 2/1982 | Royer | 435/68.1 |
| 4,395,399 | 7/1983 | Ovchinnikov et al. | 520/322 |
| 4,719,289 | 1/1988 | Kolar et al. | 536/18.7 |
| 4,806,473 | 2/1989 | Johansen et al. | 435/68.1 |
| 4,874,813 | 10/1989 | O'Shannessy | 530/395 |
| 4,925,796 | 5/1990 | Bergh et al. | 435/68.1 |
| 5,180,674 | 1/1993 | Roth | 435/97 |
| 5,246,840 | 9/1993 | Nilsson | 435/74 |
| 5,262,312 | 11/1993 | Holla et al. | 435/101 |
| 5,278,299 | 1/1994 | Wong et al. | 435/193 |
| 5,288,637 | 2/1994 | Roth | 435/97 |

*Primary Examiner*—Herbert J. Lilling
*Attorney, Agent, or Firm*—Welsh & Katz, Ltd.

[57] ABSTRACT

A process for the synthesis of a glycopeptide using a solid phase matrix is disclosed. The matrix is compatible with aqueous and organic solvents and is comprised of a silica-based solid support to which is linked a two-part spacer group having a chain length of about 12 to about 40 methylene groups. The first part of the spacer is covalently bonded to the silica-based support and has a length of about 3 to about 10 methylene groups. The second spacer part is covalently bonded to the first part of the spacer and comprises the distal end of the two part spacer. The second part is soluble as a free molecule in each of water, dimethylformamide and dichloromethane and has a terminal amine or hydroxyl group to which the C-terminal residue of the peptide portion of the glycopeptide chain is bonded. The chain of atoms connecting the desired glycopeptide to the solid phase matrix also includes a moiety having a selectively severable bond which on cleavage of that bond separates the matrix from whatever else is bonded to that moiety.

13 Claims, No Drawings

PROCESS FOR SOLID PHASE GLYCOPEPTIDE SYNTHESIS

DESCRIPTION

1. Technical Field

The present invention relates to the synthesis of glycopeptide molecules and more particularly relates to the use of organic and enzymic syntheses of glycopeptides on a solid phase matrix that is compatible with organic solvents as well as aqueous media suitable for enzyme-catalyzed reactions.

2. Background Art

Glycoproteins and their glycopeptide portions are ubiquitous in eukaryotic life forms. Three of the linkages between the sugar and peptide chains found frequently are the Asn-($\beta$GlcNAc)-Xaa-Ser motif of N-glycoproteins, the Ser($\alpha$- and $\beta$-Xyl) motif characteristic of proteoglycans of the extracellular matrix and connective tissues and the Thr($\alpha$-Man) motif that is typically present as part of the core unit of O-glycoproteins of yeasts.

The so-called selectin molecules are endothelial cell surface molecules that are involved in leukocyte trafficking in inflammatory disease states via binding to glycoprotein or glycolipid ligands expressed on leukocytes. Each selectin binds to the same glycosidic portion of the ligand; NeuAc$\alpha$2,3Gal$\beta$1,4(Fuc$\alpha$1,3)GlcNAc or sialyl Lewis$^x$ (SLe$^x$).

The E-selectin binds to a SLe$^x$-containing lipid, whereas the P- and L-selectins bind to SLe$^x$-containing proteins. See, Lasky, Science, 258:964–969 (1992). The synthesis of SLe$^x$-containing synthetic ligands that inhibit the selectin-leukocyte interaction has thus been the focus of several groups. See, for example, Nicolaou et al., J. Am. Chem. Soc., 112:3693 (1990), and Ichikawa et al., J. Am. Chem. Soc., 114:9283–9297 (1992).

The fields of protein- and nucleic acid-related chemistry and biochemistry have benefited greatly from the development of solid-phase synthesis of peptides [Merrifield, J. Am. Chem. Soc., 85:2149 (1963)] and oligonucleotides. [Caruthers, M. H. in Genetic Engineering, Stelow, J. and Holaender, A., eds., Plenum, New York, Vol. 4, Chap. 1 (1982).] In contrast, the development of solid-phase synthesis of oligosaccharides has been hampered by the lack of effective differential protection/deprotection strategy and high-yield stereoselective coupling of multifunctional carbohydrate donors and acceptors. [Eby et al., Carbohydr. Res., 39:151 and references therein (1975); Excoffier et al., Tetrahedron Lett., 50:227 (1976); Nilsson et al., J. Carbohydr. Chem., 11:265 (1992); Veeneman et al., Tetrahedron Lett., 28:6695 (1987); Frechet et al., Carbohydr. Res., 22:399 (1972); Guthrie et al., J. Chem. Soc. Commun., 2690 (1971); Douglas et al., J. Am. Chem. Soc., 113:5095 (1991)]. Only recently, this problem has been addressed with some success by Danishefsky et al., [Danishefsky et al., Science, 260:1307 (1993)], who developed a new method based on glycal chemistry.

In the process of Danishefsky et al., and reported on in Borman, C&EN, 30–33 (Jun. 7, 1993), a protected glycal is covalently linked to a cross-linked polystyrene-divinylbenzene resin by an acid-labile diphenylsilyl group. The glycal is reacted with 3,3-dimethyldioxirane to form a 1,2-anhydrosugar donor molecule. That donor is then reacted with a suitably blocked acceptor glycal in organic solvent to form a glycosideglycal having a hydroxyl at C-2 of the previous donor. That glycoside glycal can be formed into a donor 1,2-anhydro compound by further reaction with the dimethyl dioxirane and reacted with a further, protected glycal to elongate the glycoside chain.

The individual glycosylation steps are said to be stereospecific, proceeding to a glycoside corresponding to inversion at the anomeric center, forming a new $\beta$-glycosyl bond that is trans to the newly formed, adjacent C-2 hydroxyl. The stereochemistry of the 1,2-anhydrosugar donors is governed by the sugar itself so that either anomer of a given sugar cannot be readily prepared, nor can a cis-2-hydroxyl group be formed. This synthesis proceeds from non-reducing terminus toward the reducing terminus of the oligosaccharide.

Zahavi et al., Carbohydr. Res., 124:23–34 (1983) and Zahavi et al., Carbohydr. Res., 228:255–263 (1992) reported the solid phase synthesis of oligosaccharides using glycosyltransferase enzymes and aminohexyl-substituted polyacrylamide gel beads as a solid support in an aqueous medium. The oligosaccharide was linked to the polymer beads by reaction of a photolabile 4-carboxy-2-nitrobenzyl glycoside with the aminohexyl group of the gel beads using 1-ethyl-3-(3-dimethylaminopropyl)carbodiimide. Additional sugars were than added to that photolabilized glycosyl group. Glycosyl transfers were less than 1 percent unless by-products were removed by ultrafiltration and the process repeated twice, under which conditions one yield of less than 8 percent was reported as maximal. This process prepares the oligosaccharide from reducing end toward non-reducing end.

Roth U.S. Pat. No. 5,180,674, reported on in Borman, C&EN, 24–27 (Mar. 29, 1993), discloses a process by which oligosaccharides are said to be prepared as a way to isolate glycosyltransferases from appropriate tissue samples. In accordance with that disclosure, a saccharide acceptor is bound to a solid support as an affinity sorbant. A tissue preparation thought to contain a desired glycosyltransferase is contacted with the affinity sorbant to bind the enzyme to the sugar. Thereafter, the postulated enzyme/sugar-support is contacted with an appropriate donor sugar nucleotide solution, which was said to lead to coupling of the two sugars and release of the desired enzyme. The formed disaccharide was said to then be useful as an affinity sorbant to capture another glycosyltransferase, which on binding could be used to add another sugar, and so on. No data showing the usefulness of that method was taught, and no method was taught for releasing the oligosaccharide from the support. That process also builds the oligosaccharide from reducing end toward non-reducing end.

Interestingly, the above process was disclosed as a method for obtaining a desired glycosyltransferase. The obtained glycosyltransferases were said preferably to be utilized immobilized, linked to supports for synthesis of oligosaccharides, with the donor, acceptor and saccharide products being free in solution. The solid and semi-solid supports disclosed for any use in that patent were a cross-linked polyacrylamide/acryloxysuccinimide (PAN) and a polymethacrylamide/methylene-bis(methacrylamide) material also containing glycidyl methacrylate and/or allyl glycidyl ether (Eupergit TM).

The use of glycosyltransferases immobilized to solid and semisolid supports in oligosaccharide syntheses are reported by several groups. David and Auge' and their co-workers have reported several such syntheses.

For example, David and Auge', *Pure & Appl. Chem.*, 59(11):1501-1508 (1987) utilized agarose gels as immobilizing supports for five enzymes, including a galactosyltransferase (EC 2.4.1.22]. Several galactosylated oligosaccharides were said to be prepared, with those authors reporting that the nature of the support used did not appear to be critical. Auge' et al., *Carbohydrate Res.*, 193:288-293 (1989) reported use of an immobilized galactosyltransferase (EC 2.4.1.90] and a solution phase sialytransferase [EC 2.4.99.1] to prepare a solution phase sialylglycopeptide with yields of 26 and 38 percents, respectively, for those two enzymatic glycosylations. That sialyltransferase was used in immobilized form on agarose gel in Auge'et al., *Carbohydrate Res.*, 200:257-268 (1990) to form solution phase sialylated oligosaccharides in 46-57 percent yields for single glycosyl transfers.

Thiem et al., *Angew. Chem. Int. Ed. Eng.*, 25:1096-1097 (1986) also reported oligosaccharide syntheses using an immobilized galactosyltransferase and other immobilized enzymes with solution phase sialyltransferase EC 2.4.99.1 to transfer the sialyl group. The solid support used in that work was said to be an aminopropyl silica gel linked to the enzymes by glutaraldehyde so that each linkage contained two waterlabile Shiff base bonds. The yield for the one-step immobilized enzyme-catalyzed transfer was said to be 30 percent, with the free sialyltransferase providing a 52 percent yield of the trisaccharide product.

Several additional methods are available for solid-phase glycopeptide synthesis. None of them involves the use of glycosyltransferase in solid-phase synthesis [Kunz, *Angew. Chem. Int. Ed. Engl.*, 26:294 (1987); Paulsen et al., *Liebigs Ann. Chem.*, 1165, (1990); Christiansen-Brams et al., *J. Chem. Soc. Perkin Trans I*, 1461 and references cited (1993); Kunz, *Pure & Appl. Chem.*, 65:1223 (1993); Otvos et al., *Tetrahedron Lett.*, 41:5889 (1990), and references therein; Chadwick et al., *Biochem. Soc. Trans.*, 19.:406S (1991); Unverzagt et al., *J. Am. Chem. Soc.*, 112:9308 (1990); Thiem et al., *Angew. Chem. Int. Ed. Engl.*, 29:80 (1990); and Schultz et al., *Tetrahedron Lett.*, 33:5319 (1992).

More recently, Wong et al., *J. Am. Chem. Soc.*, 115:5894-5901 (1993) reported liquid phase synthesis of glycopeptides in aqueous or aqueous/dimethylformamide (3:7-7:3 v/v) solutions. N-Blocked peptide or amino acid ester acyl donors were condensed with N-terminal-amino C-terminal-amido amino acids or peptide acyl acceptors using subtilisin BPN', BPN' 8397 and a thiosubtilisin derived therefrom. Either donor or acceptor could contain an O- or N-linked glycoside at any residue position other than that at which the peptide bond was formed; i.e. the $P_1$ position. Once formed, the glycosylpeptide dissolved in an aqueous medium could be further glycosylated.

Several glycopeptides containing 3-5 different amino acid residues and one or two glycosyl groups were reported as being successfully coupled with yields for the peptide-glycopeptide coupling step ranging from about 25 to about 65 percents. The synthesis of a tetrasaccharide (sialyl Lewis$^x$)-containing decapeptide was subsequently reported [Borman, *C&EN*, 25-26 (Aug. 2, 1993 ) ].

In view of the great amount of activity in this field and the importance of glycopeptides in biological systems, it would be of import if one could improve the techniques of glycopeptide synthesis by enhancing yields still further by using the organic solvents of modern peptide synthesis methods in a system that is also compatible with aqueous media that are required for use in enzymatic glycosylation reactions that provide stereospecificity. The invention described below provides one such process.

BRIEF SUMMARY OF THE INVENTION

The disclosure that follows describes a process that enables a rapid iterative formation of peptide bonds chemically or enzymatically and the enzymatic formation of glycosidic bonds on a single silica-based solid matrix that is compatible with both organic and aqueous solvents. The solid matrix includes a spacer group bonded at one end to the silica and at the other to a group that contains a selectively cleavable bond so that once prepared, the glycopeptide products can be released. No protection of the sugar hydroxyl groups is typically required.

Thus, a process for the in vitro synthesis of a glycopeptide is contemplated. That process comprises the steps of:

(a) providing a particulate solid matrix comprising a silica-based solid support having a plurality of two-part spacer groups covalently linked to the surface of the particles. The spacer groups have a proximal end and a distal end and a total chain length equal to the length of about 12 to about 40 methylene groups. The proximal end of a spacer group includes the first part of the spacer and provides the covalent link to the particles. The distal spacer group end includes the second part of the spacer, and has a terminal amine or hydroxyl group. The first spacer part has a length equal to the length of 3 to about 10 methylene groups and is covalently linked to the second spacer part. The second spacer part has a length equal to the length of about 9 to about 30 methylene groups. The second spacer part is soluble as a free molecule in each of water, dimethylformamide and dichloromethane.

In the next step, (b), the α-carboxyl group of zero to about five amino acid residues is coupled to the terminal amine or hydroxyl group of the spacer group to provide a terminal free amine. When coupled, several amino acid residues can be joined as a unit, or individually.

Thereafter, (c), a moiety having a selectively severable bond is coupled to the free amino or hydroxyl group (i) of the solid matrix when zero residues are added in step (b) or (ii) of an α-amino group of an amino acid residue coupled in step (b) to form a selectively severable matrix. The moiety also includes a second reactive functional group such as an amino or hydroxyl group in addition to the group that forms the selectively severable bond. Breaking of the selectively severable bond frees the solid matrix from the ultimately produced glycopeptide.

Next, (d), the α-carboxyl group of zero to about five amino acid residues is coupled to the second functional (amino or hydroxyl) group of the selectively severable matrix to provide an N-terminal free amino group.

The α-carboxyl group of a glycosyl amino acid or glycosyl peptide containing up to about five amino acid residues is thereafter [step (e)] coupled to the amino or hydroxyl group (i) of the selectively severable matrix when zero residues are coupled in step (d) or (ii) of an N-terminal α-amino group of an amino acid residue coupled in step (d) to form a glycosyl peptide.

A further glycosyl moiety is enzymatically coupled in step (f) to the formed glycosyl peptide in an aqueous medium to form an oligoglycosyl peptide, and step (f) is repeated in step (g) zero to about five times using the same or preferably different glycosyl moiety and enzyme so that the glycosyl peptide contains two to about seven saccharide units.

The selectively severable bond is broken in step (h) to free the oligoglycosyl peptide from said solid matrix. The freed oligoglycosyl peptide is preferably recovered after breaking of the selectively severable bond.

DETAILED DESCRIPTION OF THE INVENTION

Glycosyltransferases and glycosidases have become valuable reagents for glycosylation due to their high regio- and stereo-selectivity and increasing availability via recombinant DNA technology; [Toone et al., *Tetrahedron*, 45:5365 (1989); Ichikawa et al., *Anal. Biochem.*, 202:215 (1992) (See also Nilsson U.S. Pat. Nos. 4,918,009 and 5,246,840 and Roth U.S. Pat. No. 5,180,674) however, no viable methodology has been developed for solid-phase enzymatic synthesis of oligosaccharides using these enzymes.

The present invention contemplates a process that utilizes aqueous medium-based enzymatic methods for building oligosaccharide chains combined with anhydrous organic solvent medium-based organic syntheses (chemical syntheses) or aqueous/organic solvent-based enzymatic methods to prepare oligopeptides to which the oligosaccharide chains are linked. These two very different synthesis techniques are used with a single solid phase matrix that is compatible with both anhydrous organic solvents and aqueous media that are free from the presence of organic solvents.

Thus, a process for the in vitro synthesis of a glycopeptide is contemplated. That process comprises the steps of:

(a) providing a particulate solid matrix comprising a silica-based solid support having a plurality of two-part spacer groups covalently linked to the surface of the particles. The spacer groups have a proximal end and a distal end and a chain length equal to the length of about 12 to about 40 methylene groups. The proximal end of a spacer group includes the first part of the spacer and provides the covalent link to the particles. The distal spacer group end includes the second part of the spacer, and has a terminal amine or hydroxyl group. The first spacer part has a length equal to the length of 3 to about 10 methylene groups and is covalently linked to the second spacer part. The second spacer part has a length equal to the length of about 9 to about 30 methylene groups. The second spacer part is soluble as a free molecule in water, dimethylformamide and also in dichloromethane.

In the next step, (b), the α-carboxyl group of zero to about five amino acid residues is coupled to the terminal amine or hydroxyl group of the spacer group to provide a terminal free amine.

Thereafter, (c), a moiety having a selectively severable bond is coupled to the free amino or hydroxyl group (i) of the solid matrix when zero residues are added in step (b) or (ii) the α-amino group of an amino acid residue coupled in step (b) to form a selectively severable matrix. The selectively severable moiety also includes a second reactive functional group such as an amino or hydroxyl group in addition to the functionality that forms the selectively severable bond. Breaking of the selectively severable bond frees the solid matrix from the ultimately produced glycopeptide.

Next, (d), the α-carboxyl group of zero to about five amino acid residues is coupled to the second functional group (amino or hydroxyl group) of the selectively severable matrix to provide an N-terminal α-amino group.

The α-carboxyl group of a glycosyl amino acid or glycosyl peptide containing up to about five amine acid residues is thereafter [step (e)] coupled to the amino or hydroxyl group (i) of the selectively severable matrix when zero residues are coupled in step (d) or (ii) of an α-amino group of an amino acid residue coupled in step (d) to form a glycosyl peptide.

A further glycosyl moiety is enzymatically coupled in step (f) to the formed glycosyl peptide in an aqueous medium to form an oligoglycosyl peptide, and step (f) is repeated in step (g) zero to about five times.

The selectively severable bond is broken in step (h) to free the oligoglycosyl peptide from the solid matrix. The freed oligoglycosyl peptide is preferably recovered after breaking of the selectively severable bond.

Turning to the several steps and ingredients used in a contemplated process, a key ingredient is the solid matrix, which is comprised of two parts: (i) the solid support and (ii) a two-part spacer group that is covalently linked to the solid support.

The solid support does not swell substantially in either water or other aqueous medium, as are used in enzymatic syntheses, nor does it swell substantially in organic solvents such as dimethylformamide (DMF) and dichloromethane (methylene chloride) as are utilized in anhydrous chemical peptide syntheses. The only solid supports known to the inventors having these non-swelling properties that can be used for the present syntheses are based on silica and include porous glass and silica gel. Either material may swell slightly in one solvent or another, but such swelling is minor compared to the well known swelling exhibited by usually used peptide syntheses supports such as cross-linked poly(styrene-divinylbenzene) beads or the polyacrylamide or polysugar-based supports such as agarose and Sephedex TM that have been suggested for use in aqueous systems for oligosaccharide syntheses. Silica gel is a preferred solid support because of its high surface area and the relatively high amount of functionalization that can be achieved using silica gel as compared to porous glass.

For example, four aminopropyl controlled pore glass products having different pore sizes are available from Sigma Chemical Co., St. Louis, Mo. These materials are said to have 150–250 down to 40–100 μmoles of primary amine per gram of material, with lessened activity/gram being present with increasing average pore size from 75 Å to 700 Å. Also available from Sigma and useful here, are glass products prepared from aminopropyl glass that have still lesser amounts of p-phenylenediamine and isothiocyanato groups.

A preferred silica gel solid matrix can be prepared from the aminopropyl silica gel available from Sigma that has about 1–2 mmoles of primary amine per gram of material. This material thus has about 5- to 10-times the loading capacity of the controlled pore glass product. This preferred material has a size of about 200–425 mesh and an average pore size of about 150 Å.

Silica-based matrices such as the partial matrices discussed above are prepared from a suitable silica support such as silica gel or controlled pore glass by the reaction of an organosilicon compound with the support to covalently link the first spacer part (an aminopropyl group) to the silica. These reactions are well known in the art. Amino-functional silanes having two or three $C_1$–$C_3$ alkoxy groups are particularly preferred organosilicon compounds for use in such linking reactions. Silanes having a mercapto functional group and those having an acetoxy group convertible to a hydroxyl group by aminolysis after covalent linking to the silicon-based matrix are also available and can be used.

Preferred amino-functional silanes are ω-amino-$C_1$–$C_6$-alkylenetri-$C_1$–$C_3$-alkoxy silanes. Exemplary compounds include 4-aminobutyltriethoxysilane and 3-aminopropyltrimethoxysilane. Use of aminopropyltrimethoxysilane to prepare aminopropyl silica gel as a silica-based support and first spacer part is preferred here. Other exemplary organosilanes from which the first spacer part can be prepared include N-(2-aminoethyl)-3-aminopropylmethyldimethoxysilane, (aminoethylaminomethyl)phenethyltrimethoxysilane and N-(6-aminohexyl)aminopropyltrimethoxysilane. These materials are available from Huls America, Inc., Piscataway, N.J., and their syntheses and use are discussed in *Silicon Compounds: Register and Review*, 5th ed., Anderson et al., eds., Huls America, Inc., Piscataway, N.J. (1991) and in the citations therein.

The two-part spacer group linked to the silica-based solid support is a substantially linear molecule. Some branching can be tolerated as can be the presence of one or more rings, which for 6-membered rings are preferably 1,4-substituted so that the spacer extends generally in a linear manner rather than being purposefully kinked. A spacer has an overall length of about 12 to about 40 methylene groups (as discussed below). More preferably, that length is equal to the length of about 15 to about 30 methylene groups, and most preferably about 20 to about 25 methylene groups.

Using a preferred silica gel matrix as exemplary, the distal end of the spacer is covalently linked to the silica via a siloxane such as aminopropyltrimethoxysilane that is used here to prepare aminopropyl silica gel. Other silicon derivatives as are discussed above such as aminobutyltriethoxysilane can also be used to covalently link the distal end of the spacer to the solid phase silica-based support to form the matrix.

The first part of the spacer group has a length equal to the length of about 3 to about 10 methylene groups. In more preferred practice, the first spacer part has a length of 3 to about 7 methylene groups as is the case where an ω-amino-$C_2$–$C_6$ alkylene spacer such as aminopropyl or aminobutyl is used.

A methylene group (—$CH_2$—), an oxy group (—O—) and a secondary amino group (—NH—) are all about the same size, with the bond length of a methylene-to-methylene (—$CH_2$—$CH_2$—) in an alkane being actually slightly larger than a —$CH_2$—O— or —$CH_2$—NH— bond length. However, a length based on a methylene group as is present in a $C_3$–$C_{15}$ alkane in extended form is readily ascertainable by reference to standard texts, molecule models and computer programs, and is therefore used herein as an easily ascertainable, measurement of length. A carbonyl carbon of an amide is similarly considered as if it were one methylene in length, as are the nitrogen of an amide or urea and an oxygen of an ester, carbonate or carbamate. Ethylenic and acetylenic unsaturations are considered to have the length of about two methylenes, even though the length of a double bond is about 1.3 Å, and a triple bond is about 1.2 Å, whereas a single bond is about 1.5 Å. A 1,4-disubstituted phenyl ring is deemed to have the length of a 1,4-disubstituted butylene.

Other first portions of a spacer include an N-(propylene)-p-phenylenediamine [—($CH_2$)$_3$NH—$C_6H_5$—$NH_2$] that has a length of about 9 methylene groups, propyleneisothiocyanate [—($CH_2$)$_3$NCS] that has a length of about 9 methylenes, an (aminoethylaminomethyl)phenethyl group that has a length of about 11 methylenes and an N-(2-aminoethyl)-3-aminopropyl group that has a length equal to about 7 methylene groups, and the like.

The second spacer part is covalently linked (bonded) to the first spacer part, and again is generally linear. The second spacer part has a length equal to that of about 9 to about 30 methylene groups, more preferably about 12 to about 24 methylene groups, and most preferably about 15 to about 21 methylene groups.

The end of the second spacer part not covalently bonded to the first spacer part defines the distal end of the spacer group so that the spacer group distal end includes the second part of the spacer. The distal end of the spacer group has a terminal hydroxyl, or a primary or secondary amino group, with a primary amino group being preferred.

The second spacer group part is prepared from a hydrophilic compound, which, as a free molecule, is soluble in both water and other aqueous media used in normal enzymatic reactions, as well as being soluble in anhydrous organic solvents such as DMF and methylene chloride (dichloromethane) that are used in solid phase peptide synthesis. Exemplary second spacer group parts include oligo-$C_2$–$C_3$-amino acid residue peptides, oligo-$C_2$–$C_3$-alkyleneoxyglycols, $C_2$–$C_3$-alkyleneoxyglycol or $C_2$–$C_3$-alkyleneaminoalcohol carbonates, ureas or urethanes, and mixtures thereof.

Solubility is a relative measurement as even the most insoluble materials possess some solubility in any solvent with which it can be wet. Adequate solubility here in each of water, DMF and methylene chloride can be assured by the presence of an average of about one carbonyl-containing [amide, ester, urethane (carbamate), urea or carbonate] or oxy linkage for each two to three non-carbonyl carbon atoms in the second spacer part chain, and the freedom from ionically charged species; i.e., salts, such as amines, quaternary amines, carboxylates, sulfonates and the like.

Exemplary $C_2$–$C_3$-amino acids from which a contemplated second spacer part peptide can be prepared are glycine (Gly), alanine (Ala) and β-alanine (β-Ala). Heteropeptides such as those having Gly-Ala repeating units are contemplated, as are homopeptides, with homopeptides such as an oligoglycine being preferred. An oligohomoglycine having about four to about eight glycines is preferred, with a chain of five to seven glycines being more preferred.

An oligopeptidyl second spacer part can readily be covalently joined to the first spacer part such as an aminopropyl group by usual peptide synthesis techniques such as by coupling in anhydrous DMF using an N-protected amino acid such as N-Boc-Gly in the presence of a carbodiimide such as dicyclohexylcarbodiimide (DCC) or diisopropylcarbodiimide. A nucleophilic displacement (aminolysis) of a peptide $C_1$–$C_6$ alkyl ester such as with N-Boc-Gly-Gly-Gly-$OCH_3$ with a first spacer part amino group is also contemplated.

Oligo-$C_2$–$C_3$-alkyleneoxyglycols are also contemplated second spacer group parts. Such molecules contain ethyleneoxy (—$CH_2$—$CH_2$—O—) or 2-propyleneoxy [—$CH_2(CH_3)$—$CH_2$—O—] repeating units that are terminated by hydroxyl groups. These materials are commonly referred to as polyethylene glycol (PEG) and polypropylene glycol (PPG), respectively. They are commercially available in a wide range of molecular weights. For example, diethylene glycol, triethylene glycol and PEG molecule mixtures having average molecular weights of 200, 300 and 400 that correspond to an average of about 4, 6.4 and 8.7 repeating units, respectively, are available from Aldrich Chemical Co., Milwaukee, Wis., as are dipropylene glycol and PPG molecules having an average of about 7 and about 12 repeating units.

A PEG or PPG molecule constituting a second spacer group part can be covalently bonded to a first spacer group part by reaction with a before-mentioned silica-bonded propylene isothiocyanto group, which forms a thiourethane linkage with the PEG or PPG molecule. The use of mono- and di-amine-terminated oligoalkyleneoxy compounds as second spacer group portions is also contemplated. These commercially available compounds can be similarly linked to the solid support via an isothicyanato group.

Second spacer group parts (portions) containing one or more urea, urethane or carbonate linkages are also contemplated. Exemplary compounds here include $C_2$–$C_3$-alkyleneoxyglycol carbonates such as dihydroxyethyl carbonate [($HOCH_2CH_2O$—$)_2CO$], $C_2$–$C_3$-alkyleneaminoalcohol ureas such as dihydroxyethyl urea [($HOCH_2CH_2NH$—$)_2C(O)$], and dihydroxyethyl urethane [($HOCH_2CH_2OC(O)NHCH_2CH_2OH$], and diaminopropylurea [($NH_2CH_2$—$CH_2$—$CH_2$—$NH$—$)_2$-$C(O)$]. Each of the above compounds can be dimerized by reaction of two moles of each with one mole of phosgene in the presence of an appropriate base to neutralize the formed hydrochloric acid or by reaction (transesterification) with one mole of dimethyl carbonate. Mixed "dimers" containing each type of linkage can also be formed and used.

Each of the amine- or hydroxyl-terminated carbonate, urethane or urea compounds is itself readily prepared by appropriate reaction with phosgene, methyl chloroformate or dimethyl carbonate. Each can also be covalently bonded (linked) to the first portion via an isothiocyanato group, or by linkage to an amine such as a propyleneamine via prior reaction with a diacid such as succinic, maleic, or glutaric acids. Each of the above reactions being well known to skilled workers, as is the appropriate removable blocking of a terminal amine or hydroxyl group so that only one end of the second part of the spacer reacts with the first part.

As should be apparent from the above discussion, after covalent bonding of the two parts of the spacer, the distal end of the spacer contains functional group that is reactive with a carboxyl group; i.e., an amine or a hydroxyl group. In some instances, a group such as an amine of an oligopeptide is blocked with a selectively removable protecting group such as Boc of Fmoc that can be readily removed for reaction with a carboxyl group.

When assaying the water-solubility of a second spacer group part, compounds containing amines as free molecules are assayed as their N-acetyl derivatives. Carboxyl-containing second spacer parts are assayed as carboxamides. For example, the tripeptide second spacer part Gly-Gly-Gly is assayed as N-acetyl-Gly-Gly-Gly-$NH_2$ for solubility.

Without wishing to be bound by theory, it is thought that use of a spacer whose second part is soluble in each of water, DMF and methylene chloride as disclosed here permits the growing peptide chain and then oligoglycosyl portion to be solvated and extend away from the surface of the support in each solvent utilized. It is further thought that water solubility of that part of the spacer permits the glycosylating enzyme to encompass one or more sugar rings, the peptide and part of the spacer.

The α-carboxyl group of zero to about five amino acid residues is coupled to the terminal hydroxyl or amine group of the spacer group in step (b). Thus, no residues need be added. In the alternative, a peptide chain of up to about five residues can be added to the spacer.

The added residues can be added individually using standard anhydrous peptide synthesis technology as is well known in the art. The added residues can also be added as a premade peptide of two to about five residues using anhydrous chemical methodology.

A similar peptide can also be added in an aqueous or an aqueous/organic solvent mixture such as water/DMF as an amino-terminal-blocked, carboxy-terminal-$C_1$–$C_6$ alkyl ester using subtilisin BPN', subtilisin BPN' variant 8397 or the thiosubstilisin derived from variant 8397 prepared by Cys 206→Gln 206 (C206Q) mutation followed by conversion of the active site Ser to Cys, as is described in Wong et al., *J. Am. Chem. Soc.*, 115:5893–5901 (1993). These enzymes can link substantially any peptides together via an N-blocked C-$C_1$–$C_6$-alkyl ester donor peptide and an N-amino acceptor peptide. However, peptides having a Pro at the $P_1'$ position do not appear to couple, and those having Leu, Ile or Val at $P_1'$ react slowly.

The added amino acid residue or peptide can be any of the naturally occurring residues or an unnatural residue such as ornithine, hydroxyproline or a D-isomer where usual organic synthesis in anhydrous solvents is utilized. Where an added residue is a $C_2$–$C_3$ amino acid residue that can also be a part of the spacer group, the residue(s) is deemed to be part of the spacer so long as the total length limitations of the spacer group and its second part are maintained. Where a $C_2$–$C_3$ amino acid residue or peptide containing one or more such residues at the N-terminus is added and that addition provides a chain length longer than that permitted by the before-discussed length limitations, the added peptide or residue is deemed to be part of the growing peptide chain. In preferred practice, zero amino acid residues are added to the spacer and step (b) is omitted.

Where such a residue or peptide is added, however, an N-terminal selectively removable blocking group such as Boc, Fmoc or Cbz is typically present during synthesis. That blocking group, when present is removed to provide a free α-amino group to carrying out the next synthesis step.

The next step in the process is the coupling to the matrix of a moiety that contains a selectively severable bond. Where zero amino acid residues are added to the spacer of the matrix, that moiety is added to the hydroxyl or amino group at the distal terminus of the spacer. When one or more residues is added in step (b), the selectively severable bond-containing moiety is coupled to above-described free α-amino group.

The moiety containing a selectively severable bond also includes an amine or hydroxyl group that is typically blocked during synthesis, as discussed before.

Removal of the blocking group permits further coupling of the glycosyl peptide units to the matrix. The selectively severable bond and amine or hydroxyl group of this moiety can thus be arrayed so that the selectively severable bond is proximal to the matrix and the amine or hydroxyl group is proximal to the peptide portion of the glycopeptide; i.e., distal to the matrix, or vice versa.

The selectively severable bond that is added is present in the growing chain from the spacer toward the glycosyl peptide that is ultimately prepared. Breaking (severing or cleaving) that selectively severable bond breaks that chain, thereby freeing the solid matrix and any joined atoms between the matrix and severable bond from anything bonded to that moiety; i.e., the ultimately produced glycopeptide.

The use of a moiety containing one of several types of well known selectively severable bonds is contemplated.

In one preferred embodiment, the coupled moiety contains an amino acid residue or sequence that is specifically recognized and cleaved by a hydrolyric enzyme. Exemplary of this type of selectively severable bond-containing moiety is a phenylalanyl-residue such as the phenylalanyl glycolate [Phe-OCH$_2$C(O)] utilized herein that is specifically recognized and readily hydrolyzed by α-chymotrypsin. Where the spacer group is terminated at its distal end by a hydroxyl group and no amino acid residues are coupled in step (b), the phenylalanyl residue can be coupled directly to that terminal hydroxyl to form the selectively severable phenylalanyl ester. The α-amino group of the Phe residue provides a functional group for linkage to the peptide.

Further peptidyl sequences that can be utilized for the moiety containing a selectively severable bond include those recognized and cleaved by the serine protease blood Factor Xa, as well as that recognized and cleaved by thrombin, or other protease enzymes such as trypsin, pepsin and elastase. These enzymes are commercially available. Their peptide recognition and cleavage sites are well known, as is their use in selective cleavage of peptides and proteins so no more need be said here about them.

Photocleavable moieties are also contemplated. One such moiety is a o-nitrobenzyl ester or ether group as was used in Zehavi et al., *Carbodhvd. Res.*, 228:255–263 (1992); albeit those authors used their clearable moiety bonded directly to a glycosyl group. See also, Green et al., *Protective Groups in Organic Synthesis*, 2nd ed., John Wiley & Sons, Inc., New York (1991), pages 257–258. In one embodiment, an N-blocked amino acid α-carboxyl group is ester bonded to the hydroxyl of 2-nitro-4-carboxybenzyl alcohol and the carboxyl of the nitrobenzyl group is coupled to the free amine or hydroxyl of the spacer or intervening amino acid residue or peptide. Here, irradiation and cleavage of the o-nitrobenzyl ester bond after preparation of the glycopeptide, which includes the amino acid esterified to the photolabile group, provides a free glycopeptide and a matrix linked to the substituted benzaldehyde resulting from the photochemical reaction.

In another embodiment, an N-blocked 2-nitro-4-aminobenzyl C$_2$–C$_6$ dicarboxylic acid half-ester such as 2-nitro-4-N-Boc-aminobenzyl half-succinate is coupled to the hydroxyl or amino group of the spacer or peptide. Removal of the N-blocking group provides an amine for subsequent peptide synthesis. Irradiation and cleavage of this selectively severable bond after preparation of the glycopeptide leaves the substituted benzaldehyde coupled to the glycopeptide and is therefore less preferred.

Yet another type of selectively severable bond is a disulfide bond of a mixed disulfide that can be cleaved by reaction with mercaptans such as dithiothreitol, thioglycolic acid and the like, or by mild reducing agents such as sodium borohydride. An exemplary moiety of this type is N-Boc-2aminoethylcarboxymethyl disulfide (Boc-HNCH$_2$CH$_2$S—SCH$_2$CO$_2$H) whose carboxyl can be coupled to the spacer amine or hydroxyl and whose amine, after deprotection, can be used as part of the glycosyl peptide chain. Cleavage of this selectively severable bond after glycopeptide synthesis provides a glycopeptide whose C-terminal residue has an amido-linked ethyl mercaptan, whose mercapto group can be used to link the glycopeptide to an immunogenic carrier or other protein for preparation of antibodies to the glycopeptide or as part of a protein conjugate in immunoassays.

The α-carboxyl group of zero to about five amino acid residues is coupled to the amino or hydroxyl group of the moiety with a selectively severable bond in step (d). Thus, again, no residues need be coupled at this step. It is preferred, however, that at least one amino acid residue be added, typically as an N-blocked residue or peptide, at this step, with the blocking group being removed prior to the next step to provide a free α-amine.

As noted before, N-blocked amino acid residues can be added individually using usual anhydrous solvents as is typical for solid phase peptide synthesis. This type of synthesis is preferred because of its high, substantially quantitative yields. A plurality of amino acids can also be added as an N-blocked peptide or N-blocked peptide carboxy-terminal C$_1$–C$_6$ ester, using the anhydrous solution chemistry used to add individual residues, or with an enzyme in an aqueous or a mixed aqueous/organic solvent medium as discussed before and in Wong et al., *J. Am. Chem. Soc.*, 115:5893–5901 (1993).

The α-carboxyl group of a glycosyl amino acid or glycosyl peptide containing up to about five amino acid residues is coupled in step (e) to either (i) the hydroxyl or amino group of the moiety containing the selectively severable bond when zero amino acid residues are coupled in step (d), or (ii) the deblocked α-amino group of the N-terminal amino acid residue coupled in step (d).

Thus, at least one amino acid residue must be coupled in this step, and where only one residue is coupled, that residue contains a glycosyl group. The amino acid residue(s) coupled at this step can be coupled individually using chemical techniques and anhydrous solvents, and that method of synthesis is preferred.

As is illustrated in the before-cited Wong et al., *J. Am. Chem. Soc.*, 115:5893–5901 (1993) disclosure, an N-blocked glycosyl peptide carboxy-terminal C$_1$–C$_6$ alkyl ester can also be used as an acyl donor in an enzymatic coupling with subtilisin BPN', or the BPN' 8397 variant or the thiosubtilisin variant of BPN' 8397 using an aqueous medium or an aqueous/organic solvent medium. The glycosyl group is preferably located on a residue whose acyl group does not undergo the amide-forming reaction; i.e., the glycosylamino acid residue is preferably not at the P$_1$ position. An enzyme can transfer a β-linked xylyl-Ser group, but not an α-linked xylyl-Ser or a triacetylGlcNAc-Asn at the P$_1$ position.

The glycosyl portion of a glycosyl amino acid that is coupled can be substantially any glycosyl group that is an acceptor for a glycosyl transferase or glycosidase, as are discussed hereinafter. The glycosyl group must therefore contain at least one free hydroxyl group or a hydroxyl group that is blocked by a selectively removable protecting group that is removed prior to coupling of another glycosyl (saccharide) group.

It is preferred that all of the hydroxyl groups of the glycosyl group be unprotected, free hydroxyl groups. Indeed, the use of a glycosyl-substituted amino acid whose glycosyl hydroxyl groups are unprotected in a contemplated synthesis, particularly when chemical synthetic methods that utilize anhydrous solvents are employed, is a salient feature and unexpected benefit of this invention. Any other functional groups such as carboxyl, amino and mercapto, if present on a glycosyl group are blocked with a readily removable blocking group such as a Boc group for an amine or a benzyl ester for a carboxyl as are well known, or are protected with a substantially non-removable group such as an N-$C_1$-$C_6$ acyl as in N-acetyl glucosamine (GlcNAc) or sialic acid (NeuAc).

Preferred glycosyl amino acids are the N- and O-linked glycosides that are found in nature such as N-Asn(GlcNAc), O-Ser(Xyl) and O-Thr(Man) and O-Ser(GalNAc) or O-Thr(GalNAc). Both α- and β-configured glycosides are contemplated. These glycosyl amino acid derivatives are known, and exemplary syntheses of several N- and O-linked glycosylated amino acid methyl esters are described in Wong et al., *J. Am. Chem. Soc.*, 115:5893-5901 (1993) and the citations therein. Other desired glycosides can be similarly prepared, and the free carboxylic acid forms of those glycosyl amino acid derivatives can be readily prepared by hydrolysis in base, followed by appropriate neutralization.

Exemplary glycoamino acid residues and glycopeptides that can be transferred enzymatically are illustrated below. These materials were prepared as discussed in Wong et al., *J. Am. Chem. Soc.*, 115:5893-5901 (1993).

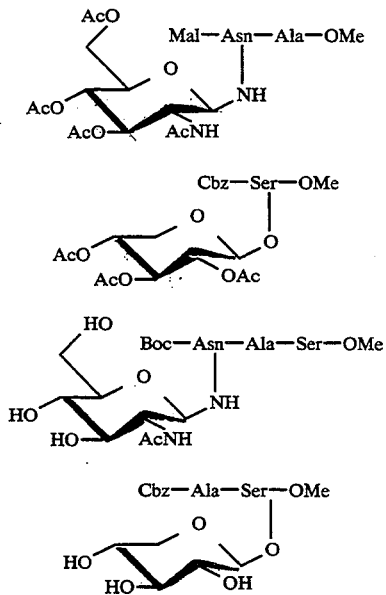

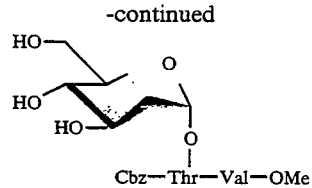

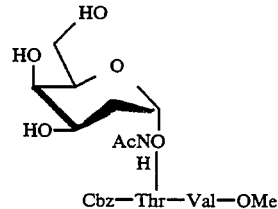

In the above formulas, Ac=acetyl; Mal=maleic half-amide; Me=methyl; Boc=t-butyloxycarbonyl; Cbz=carbobenzoxy.

The use of C-linked glycosylamino acids and peptides containing the same is also contemplated herein. Such amino acid derivatives are also known or can be prepared by analogy to known syntheses, and thus, need not be discussed further.

If desired, another zero to about five further amino acid residues can be coupled to a matrix-linked glycopeptide that contains a single glycosyl group. Again, the amino acid residues can be added individually using usual solid phase peptide synthesis chemistry. Two to about five residues can also be linked as a peptide unit via a before-discussed enzyme, so long as the glycosyl group is not at the $P_1$ position, as discussed before. Where one or more further amino acid residues are to be coupled to the matrix-linked glycopeptide using organic chemical methods, it is preferred that the glycosyl hydroxyl groups be protected with a removable protecting group such as an O-$C_1$-$C_6$ acyl group like an acetyl group.

At least one further glycosyl moiety is thereafter enzymatically coupled to the glycosyl group of the glycosyl peptide to form an oligoglycosyl peptide. These enzymatic reactions are carried out in an aqueous medium or a substantially aqueous medium that contains up to about 15 percent, and preferably less organic solvent.

Up to a total of about seven saccharide units, each glycosidically linked to the others except for one at the reducing terminus that is glycosidically linked to the peptide chain, can be present in the prepared glycopeptide. A total of about two to about five, and more preferably about three to about four saccharide units are present in the glycopeptide. Thus, after the second glycosyl moiety is enzymatically coupled to the peptide-linked glycoside, enzymatic-glycoside coupling is repeated zero to about five times using the same glycosyl moiety and enzyme, same glycosyl moiety and different enzyme, or a different glycosyl moiety and enzyme. It is preferred that different glycosyl moieties and enzymes be used for each coupling.

Enzymatically-catalyzed oligosaccharide (oligoglycoside) synthesis involves a complex interrelation between the structure of the saccharide to be glycosylated (the acceptor), the added glycosyl group (the donor) and the enzyme that catalyzes glycosylation. An enzyme typically only catalyzes the addition of one glycosyl group (saccharide unit) to one or a few acceptors, with that addition being stereo- and regiospecific.

The enzymes that catalyze such additions are referred to as glycosyltransferases.

In mammalian systems, eight donor saccharides, present as nucleotide mono- or diphosphates (activated sugar nucleotides), are acted upon by glycosyltransferases in the so-called Leloir pathway to produce most of the oligo- and polysaccharides present. Those eight saccharides are Glc, GlcUA, GlcNAc, Gal, GalNAc, Man, Fuc and NeuAc. Microorganisms and plants utilize saccharide nucleotide phosphate building blocks similarly, employing still further sugars and saccharides.

Glycosyltransferase enzymes are classified, named and numbered under the auspices of The International Union of Biochemistry and Molecular Biology (IUBMB). Enzymes recognized are listed in *Enzyme Nomenclature* 1991, Academic Press, Inc., San Diego, (1992). That volume lists about 250 glycosyltransferases, although not all of the listed enzymes transfer glycosyl groups to saccharides. Glycosyl transferases are given the class designations E.C. 2.4.1. for hexosyltransferases, 2.4.2. for pentosyltransferases, and 2.4.99. for transferring of other glycosyl groups, with a further digit(s) to identify a specific enzyme having a specific activity. With that nomenclature system, several different enzymes having those same general activities can and do have the same E.C. number. In addition to the enzymes listed, still further glycosyltransferase enzymes are continually being isolated and reported in the literature.

Glycosidase enzymes normally function to cleave O-, N- or S-glycosyl bonds. However, by careful adjustment of donor and substrate concentrations or by trapping reaction products, several glycosidases can be used to form rather than to break glycosyl bonds. See, for example, Nilsson U.S. Pat. Nos. 4,918,009 and 5,246,840. Glycosidases that hydrolyze O-glycosyl compounds are given the class designations E.C. 3.2.1., and over 130 such enzymes are listed in *Enzyme Nomenclature* 1992, above.

A process of the present invention utilizes the benefits of solid phase synthesis technology along with the substrate, regio- and stereospecificities of glycosyltransferases and glycosidases to synthesize oligoglycosyl (oligosaccharide) portions of a desired glycopeptide. Unless a specific enzyme or enzyme class is stated, a glycosyltransferase- or glycosidase-catalyzed reaction is referred to herein as an enzymatic coupling, an enzyme-catalyzed coupling or a similar phrase. The use of a glycosyltransferase is, however, preferred.

A contemplated enzyme typically recognizes only one or a few saccharide residues at or near the non-reducing terminus of a substrate acceptor. As a consequence, a glycosyltransferase, for example, that in nature transfers a particular saccharide to a particular hydroxyl of a particular substrate because of the cellular location of that enzyme, can be used to transfer the same donor saccharide to the usual hydroxyl in an acceptor saccharide substrate whose non-reducing terminus is the same as that of the natural substrate, but whose reducing terminus is quite different. For example, the $\alpha$2,3-sialyltransferase (E.C. 2.4.99.6) that normally transfers a sialic acid (NeuAc) group to a terminal 3-hydroxyl of an acceptor Gal$\beta$1,4-GlcNAc substrate moiety in a glycoprotein can also be used to transfer a NeuAc group to the same acceptor Gal$\beta$B1,4-GlcNAc substrate moiety bonded directly to a peptide rather than to a protein.

Thus, by proper combination of a donor activated sugar, enzyme and glycosyl substrate, one can mimic nature and form naturally occurring glycosyl linkages using other than the native glycosyl substrate. This point is underscored by the fact that although acceptor specificity is usually quite high, if the native acceptor or a molecule having a non-reducing terminus identical to that normally glycosylated is not present and another similarly structured acceptor is present, that latter substrate can often be glycosylated as is known from the literature.

An example of this latter phenomenon is illustrated in Wong et al., *J. Am. Chem. Soc.*, 115:5893–5901 (1993). There, a Cbz-Ala-Ser($\beta$-Xyl)-OMe glycopeptide was galactosylated with the bovine enzyme galactosyltransferase (E.C. 2.4.1.22) that normally couples a galactosyl group $\beta$1,4 to an acceptor GlcNAc ring, or in the presence of $\alpha$-lactalbumin, as in that paper, to an acceptor Glc group.

In addition to the list of glycosyltransferases noted in *Enzyme Nomenclature* 1992, discussed before, Beyer et al., *Adv. Enzymol.*, 52:23–175 (1981) lists several enzymes that had been reported to that date of publication for vertebrate and primarily mammalian conjugates. The table below exemplifies several of those enzymes classed by the glycosyl group transferred and the structures formed using a particular enzyme.

TABLE

I. Sialyltransferase
 Sia$\alpha$2,6Gal
 Sia$\alpha$2,3Gal
 Sia$\alpha$2,6GalNAc
 Sia$\alpha$2,6GlcNAc
 Sia$\alpha$2,8Sia
 Sia$\alpha$2,4Gal
 Sia$\alpha$2,4GlcNAc
 Sia$\alpha$2,6Man II. Fucosyltransferase
 Fuc$\alpha$1,2Gal$\beta$
 Fuc$\alpha$1,4GlcNAc$\beta$
 Fuc$\alpha$1,3GlcNAc$\beta$
 Fuc$\alpha$1,3Glc
 Fuc$\alpha$1,6GlcNAc$\beta$
 Fuc$\alpha$1,6Gal$\beta$
 Fuc$\alpha$1, 3Gal$\beta$
 Fuc$\alpha$1, 3Fuc III. Gal actosyltransferase
 Gal$\beta$1,4Glc
 Gal$\beta$1,4GlcNAc
 Gal$\beta$1,3GlcNAc
 Gal$\beta$1,3diglyceride
 Gal$\beta$1,6GlcNAc
 Gal$\beta$1,3GalNAc
 Gal$\beta$1,6GalNAc
 Gal$\alpha$1,3GalNAc
 Gal$\alpha$1,3Gal
 Gal$\alpha$1,4Gal
 Gal$\beta$1,4Gal
 Gal$\beta$1,6Gal
 Gal$\beta$1,4Xyl IV. N-Acetylgalactosaminyltransferase
 GalNAc$\alpha$1,3Gal$\beta$
 GalNAc$\beta$1,4Gal
 Iduronic Acid
 GalNAc$\beta$1,3Gal
 GalNAc$\alpha$1,3GalNAc (GalNAcβ1,4GluUAβ1,3)$_n$
(GalNAcβ1,4IdUAα1,3)$_n$ V. N-Acetylglucosaminyltransferase
    GlcNAcβ1,4GlcNAc
    GlcNAcβ1,2Man
    GlcNAcβ1,4Man
    GlcNAcβ1,6Man
    GlcNAcβ1,3Man
    GlcNAcβ1,3Gal
    GlcNAcβ1,4Gal
    GlcNAcβ1,6Gal
    GlcNAcα1,4Gal
    GlcNAcα1,4GlcNAc
    GlcNAcβ1,6GalNAc
    GlcNAcβ1,3GalNAc
    GlcNAcβ1,4GlcUA
    GlcNAcα1,4GlcUA
    GlcNAcα1,4IdUA Glycosyl coupling with a glycosyltransferase requires the enzyme, an acceptor substrate, and an activated sugar nucleotide. These reactions are carried out in aqueous buffers, typically at a temperature of about 15° to about 40° C., at atmospheric pressure, and at a pH value and osmolality that do not inhibit the activity of the enzyme. Each of those requirements is well known in the literature, or can be readily ascertained by a skilled worker.

As noted before, glycosidase enzymes normally cleave glycosyl bonds rather than form them. However, the reaction can be made to proceed toward glycosylation rather than toward cleavage of the formed product by use of a high concentration of a donor present as a p-nitrophenyl, $C_1$-$C_6$ alkoxy glycoside or inexpensive glycoside such as lactose for transfer of a Gal group, relative to the acceptor substrate. This forward reaction can also be assisted by the presence of an appropriate glycosyltransferase and donor activated sugar nucleotide to react with the product formed by the glycosidase enzyme, and thereby drive the reaction toward glycosylation. See, for example, Nilsson U.S. Pat. No. 5,246,840. An exemplary reaction is illustrated below in Scheme 1 using β1,4galactosidase [E.C. 3.2.1.23] as the glycosidase and α2,3sialyltransferase [E.C. 2.4.99.6] as the glycosyltransferase used to drive the reaction forward, with lactose as the source of galactose.

Scheme 1

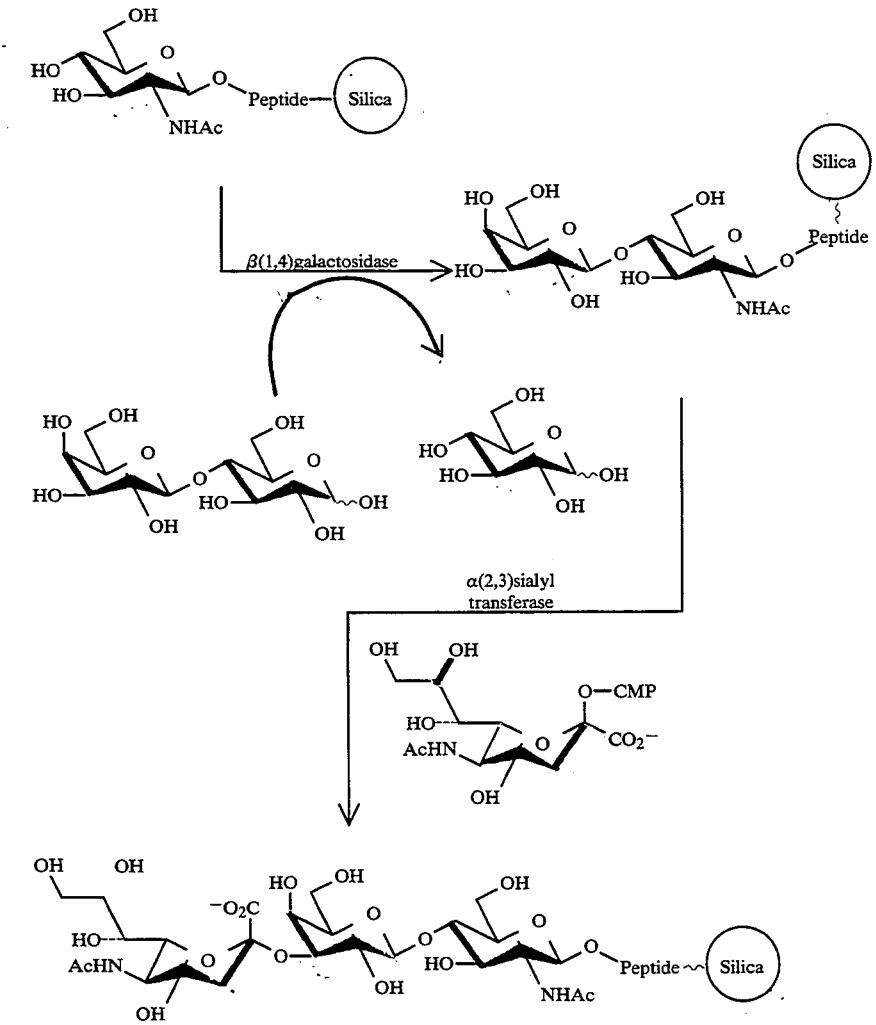

Rather than simply using a desired amount of sugar nucleotide with its glycosyltransferase, it is preferred to use a sugar nucleotide cycling (regenerating) system that continually makes more of the particular activated sugar nucleotide that is utilized by the glycosyltransferase. The bases for this preference are that the sugar nucleotides tend to decompose in aqueous media, they are costly and the yield of glycosylated glycopeptide can be increased using a regeneration system.

A CMP-sialic acid recycling or regenerating system is exemplary of this type of system, as similar systems for other sugar nucleotides are well known in the literature.

An exemplary CMP-sialic acid recycling or regenerating system comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP. The previously discussed α(2,3)sialyltransferase, and CMP-sialic acid synthetase [Vann et al., *J. Biol. Chem.*, 262:17556 (1987)] that forms CMP-sialic acid can also be formally viewed as part of the CMP-sialic acid regenerating system. An exemplary system is shown in part A of Scheme 2, below.

Nucleoside monophosphate kinases are enzymes that catalyze the phosphorylation of nucleoside monophosphates. Nucleoside monophosphate kinase (NMK) or myokinase (MK; EC 2.7.4.3) used in accordance with the CMP-sialic acid regenerating system are used to catalyze the phosphorylation of CMP. NMK's are commercially available (Sigma Chem. Co., St. Louis, Mo.; and Boehringer Mannheim, Indianapolis, Ind.).

A phosphate donor and a catalytic amount of a kinase that catalyzes the transfer of phosphate from the phosphate donor to an activating nucleotide are also part of the CMP-sialic acid regenerating system. The phosphate donor of the regenerating system is a phosphorylated compound, the phosphate group of which can be used to phosphorylate the nucleoside phosphate. The only limitation on the selection of a phosphate donor is that neither the phosphorylated nor the dephosphorylated forms of the phosphate donor can substantially interfere with any of the reactions involved in the formation of the sialylated acceptor saccharide. Pre-

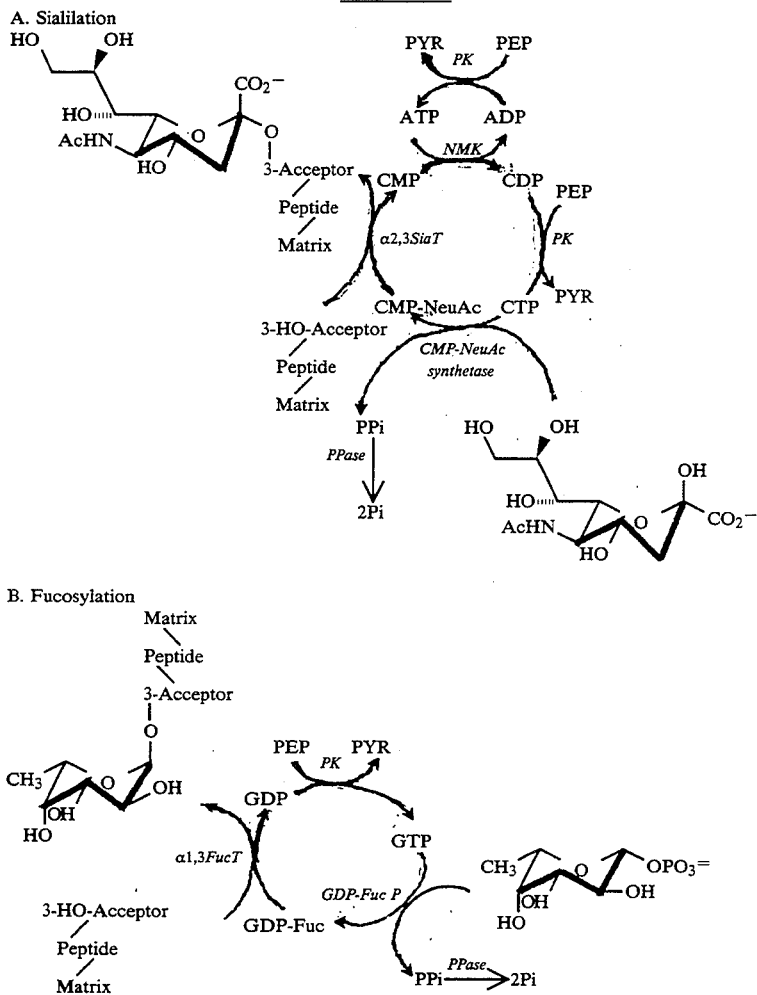

Scheme 2

A. Sialilation

B. Fucosylation

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

ferred phosphate donors are phosphoenolpyruvate (PEP) and acetyl phosphate. A particularly preferred phosphate donor is PEP.

The selection of a particular kinase for use depends upon the phosphate donor employed. When acetyl phosphate is used as the phosphate donor, the kinase is acetyl kinase. When PEP is used as the phosphate donor, the kinase is pyruvate kinase (PK; EC 2.7.1.40). Other kinases can be employed with other phosphate donors as is well known to those of skill in the art. Kinases are commercially available (Sigma Chem. Co., St. Louis, Mo.; and Boehringer Mannheim, Indianapolis, Ind.).

Because of the self-contained and cyclic character of this glycosylation method, once all the reactants and enzymes are present, the reaction continues until the first of the stoichiometric substrates is consumed.

Thus, in the sialylation example, CMP is converted to CDP, whose conversion is catalyzed by nucleoside monophosphate kinase or myokinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the matrix-linked glycosyl peptide acceptor catalyzed by $\alpha(2,3)$sialyltransferase ($\alpha$2,3SiaT), the released CMP re-enters the regenerating system to reform CDP, CTP and CMP-sialic acid. The formed PPi is scavenged as discussed below, and forms inorganic phosphate (Pi) as a byproduct. Pyruvate is also a byproduct.

As used herein, the term "pyrophosphate scavenger" refers to substances that serve to remove inorganic pyrophosphate from a reaction mixture. Inorganic pyrophosphate (PPi) is a byproduct of the preparation of CMP-NeuAc and other activated sugar nucleotides.

Produced PPi can feed back to inhibit other enzymes such that glycosylation is reduced. However, PPi can be degraded enzymatically or by physical means such as sequestration by a PPi binding substance. Preferably, PPi is removed by hydrolysis using inorganic pyrophosphatase (PPase; EC 3.6.1.1), a commercially available PPi catabolic enzyme (Sigma or Boehringer Mannheim), and that or a similar enzyme serves as the pyrophosphate scavenger.

A somewhat less complex regeneration system for fucosylation is illustrated in part B of Scheme 2. There, fucosyl-1-phosphate is transformed into the activated sugar nucleotide by reaction with GTP in the presence of GDP-Fuc pyrophasphorylase (GDP-Fuc P). Fucosylation of a matrix-linked glycopeptide acceptor using $\alpha$1,3-fucosyltransferase ($\alpha$1,3FucT) as exemplary, produces the fucosylated product and releases GDP that is recycled to GTP via PEP and pyruvate kinase. The inorganic pyrophosphate produced is again decomposed in situ using inorganic pyrophosphorylase (PPase).

In carrying out the addition of an amino acid, peptide or saccharide to a growing chain, a two phase, solid and liquid, admixture is formed. The solid phase is constituted by the matrix-linked peptide or glycopeptide, whereas the other ingredients, including enzymes are in the liquid phase. Reaction workup is consequently simplified for both peptide and oligosaccharide syntheses because the product is linked to the solid phase after each step. A product can also be cleaved from the matrix and subsequently manipulated.

Thus, the solid and liquid phases are mixed to start a reaction and are maintained in contact during the course of the reaction until a solid phase-linked product is formed. Once the reaction is over or otherwise terminated, the solid and liquid phases are separated as by filtration, centrifugation, decantation or the like, usually accompanied by one or more washing steps. The solid phase-linked product so formed can then be reacted further to link one or more amino acid residues to the peptide chain, or reacted with an appropriate sugar transferring enzyme in aqueous medium to carry out a further glycosylation and form a further solid phase-linked product that can be obtained by separating the solid and liquid phases and then cleaving the desired product from the support.

The materials present in the liquid phase such as excess amino acid from a coupling step or one or more enzymes used in glycosylation can simply be recovered for further use. For example, a multienzyme regenerating system such as that discussed in regard to Scheme 2 part A can simply be dialyzed to concentrate the enzymes and remove any small molecules. The concentrates can then be reused, freeze dried or frozen for reuse.

The concentrations or amounts of the various reactants used in this process depend upon numerous factors including reaction conditions such as temperature and pH value, and the choice and amount of acceptor saccharide to be glycosylated. Because the exemplary cyclic sialylation process permits regeneration of activating nucleotides, activated donor sialic acid and scavenging of produced PPi in the presence of catalytic amounts of the enzymes, the process is limited by the concentrations or amounts of the stoichiometric substrates free NeuAc, PEP or acceptor. The upper limit for the concentrations of reactants that can be used is determined by the solubility of such reactants.

Preferably, the concentrations of activating nucleotides, phosphate donor, acceptor saccharide and enzymes are selected such that glycosylation proceeds until the donor saccharide, e.g., sialic acid, is consumed.

By way of example, when the concentration of sialic acid is about 10.5 mM, preferred concentrations of the other non-enzyme reactants are about 1.0 mM for the $\alpha(2,3)$sialyltransferase matrix-linked acceptor glycopeptide, about 0.9 mM for CMP, about 0.09 mM for the nucleoside triphosphate (ATP) and about 46 mM for the phosphate donor (PEP). Thus, the ratio of the concentration of the two saccharides used illustratively here; i.e., sialic acid:$\alpha(2,3)$sialyltransferase acceptor is about 10:1. Lower limits for those molar ratios can be about 1:0.001, and more preferably, about 1:0.010 in the order mentioned. The CMP is present in about an equal amount to the $\alpha(2,3)$sialyltransferase acceptor, and ATP is present at about one-tenth the amount of CMP. The above relative amounts are typically used regardless of the glycosylation reaction being carried out.

Where a cyclic or regenerative glycosylation system is not utilized, the amount of activated nucleotide sugar donor is typically used in excess over the acceptor. The amount of that excess can be about 10 to about 10,000 times stoichiometric. Specific examples are provided hereinafter.

Each of the enzymes utilized in any peptide-or oligosaccharide-process herein is present in a catalytic amount. As used herein, the phrase "catalytic amount" means that amount of an enzyme at least sufficient to catalyze, in a non-rate limiting manner, the conversion of that enzyme's substrate to product.

The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The glycosylation ingredients are combined by admixture in a buffered aqueous reaction medium (solution). That buffered medium has a pH value of about 6 to about 8. The buffer is devoid of chelators that bind enzyme cofactors such as $Mg^{+2}$ or $Mn^{+2}$. The selection of a buffer is based on the ability of the buffer to maintain pH value at the desired level. Where the pH value is about 7.5, a preferred buffer is HEPES.

The reaction medium is also preferably free of solubilizing detergents and organic solvents such as methanol or ethanol, although the presence of either can be tolerated. In addition, the enzymes are preferably utilized free in solution as compared to being bound to a support such as a polymer.

The temperature at which an above process is carried out can range from just above freezing to the temperature at which the most sensitive enzyme denatures. That temperature range is preferably about zero degrees C to about 45° C., and more preferably at about 20° C to about 30° C.

The reaction mixture so formed is maintained for a period of time sufficient for the acceptor to be glycosylated to form a desired glycosylated matrixlinked glycopeptide (oligoglycosylpeptide). Some of that product can often be detected after a few hours, with recoverable amounts usually being obtained within 24 hours. It is preferred to optimize the yield of the process, and the maintenance time is usually about 36 to about 120 hours.

The produced oligoglycosylpeptide can be used without purification. However, it is usually preferred to recover the product. Standard, well known techniques for recovery of glycopeptides such as thin or thick layer chromatography, ion exchange chromatography or various types of column chromatography can be used once the glycopeptide is separated from the matrix by cleaving the selectively severable bond as discussed before. It is preferred to use one or more column chromatographic techniques for the recovery as is discussed hereinafter and in the literature cited herein.

Results

Of several solid supports examined, (styrene-and sugar-based polymers are not suitable as they tend to swell and lead to low-yield couplings) aminopropyl silica was chosen, because it (i) is compatible with both aqueous and organic solvents, (ii) has a large surface area accessible to biomolecules and (iii) has a relatively high density of functional groups (about 1.5 mmol/g) for preparative syntheses. An exemplary synthesis of an oligoglycosyl peptide that utilizes a contemplated process is illustrated in Schemes 3a and 3b below.

The aminopropyl silica is shown in the Scheme first as having its plurality of covalently-linked aminopropyl groups arrayed about the surface of a idealized particle shown in two dimensions. A narrower focus is utilized for steps (a), (b) and (c) that depicts a single aminopropyl group and its linkage to a silicon atom that is shown triply bonded to the particle surface. For steps (d) and (e), the particle and its spacer (the solid matrix) are shown simply as the circled word "silica" with a single, projecting, wavy line to highlight the coupled selectively severable bon-containing group, peptide chain and growing glycoside. The separated particulate matrix is not shown subsequent to selective cleavage or breaking of the selectively severable bond.

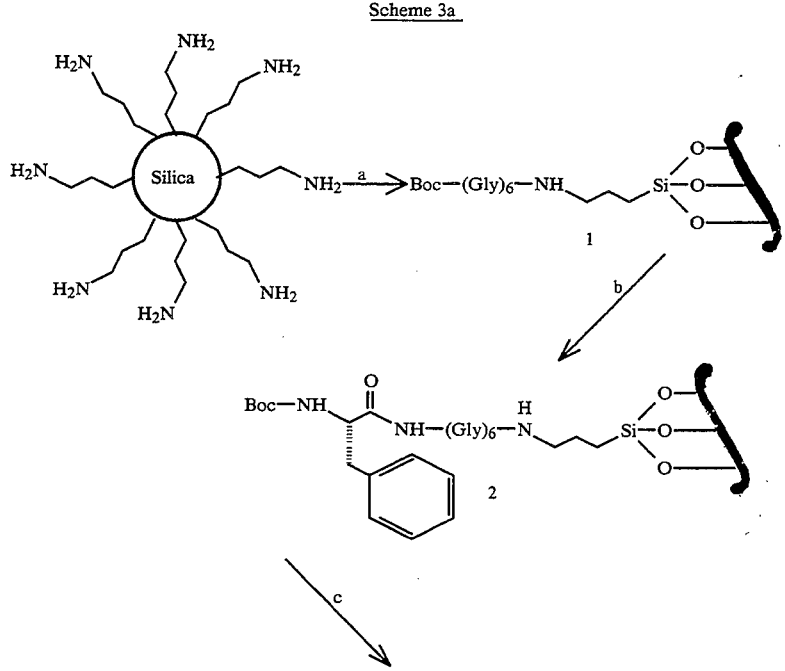

Scheme 3a

-continued

Scheme 3a

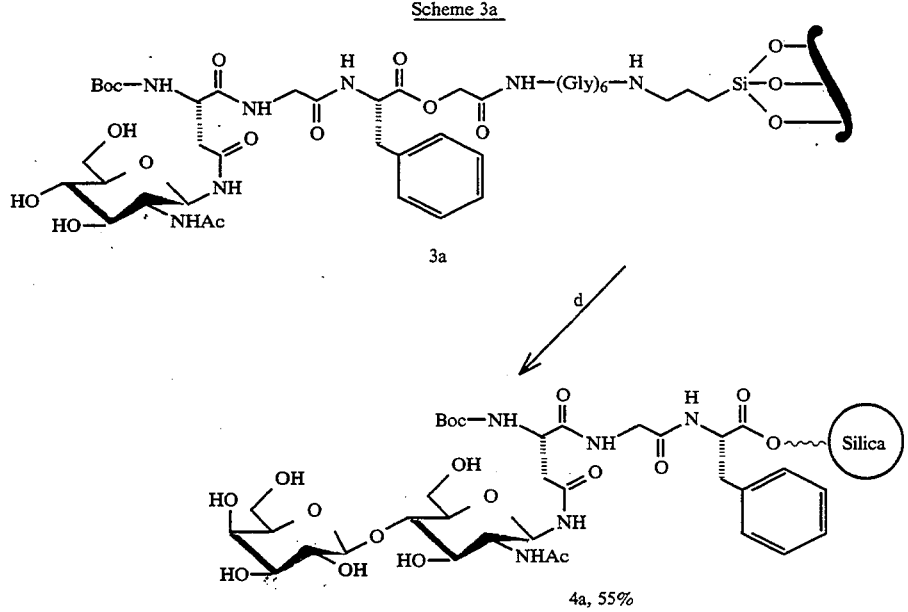

In the first step (a), a hexaglycine second spacer part was attached via two separate additions of N-Boc(-Gly)₃ to the aminopropylated solid silica support to give a substitution level of Structure 1 of 0.2 mmol/g dry silica and form the solid phase silica-based matrix. Excess amino groups were then capped using acetic anhydride, but are not shown for added clarity. The second step (b) was to implement a selective cleavage site for the release of intermediates and final products from the support under mild conditions by introduction of an α-chymotrypsin-sensitive phenylalanyl ester bond Structure 2. [α-Chymotrypsin is highly specific for substrates containing aromatic amino acid residues in $P_1$. Moreover, the specificity of serine proteases (expressed as Kcat/Km) for an ester is several orders of magnitude higher than that for the corresponding amide: Liu et al., in Boyer, P.D. Ed. *The Enzymes*, Vol. III, Academic Press: New York, 1971, pp. 609–647.] Addition of a glycopeptide [N-Boc-Asn(GlcNAcβ)-Gly] by separate amino acid couplings to the phenylalanyl α-amine in step (c) gave the glycosyl acceptor Structure 3a, which upon α-chymotrypsin-catalyzed hydrolysis yielded N-Boc-Asn(GlcNAcd)-Gly-Phe-OH (Compound 3b) as the exclusive soluble product.

β1,4-Galactosyl transfer to Structure 3a in step (d) was catalyzed by β1,4-galactosyltransferase (E.C. 2.4.1.22 Sigma) employing UDP-galactose as a glycosyl donor. Reverse-phase HPLC analysis of the supernatant after α-chymotrypsin hydrolysis of an aliquot of washed and dried solid material revealed a galactosylation level of 55 percent based on the galactosylated tripeptide Boc-Asn(Galβ1,4GlcNAcβ)-Gly-Phe (Compound 4b) isolated by semipreparative HPLC.

The subsequent solid phase α2,3-sialylation of Structure 4a of step (e) of Scheme 3b, below; was performed under similar conditions using α2,3-sialyltransferase [E.C. 2.4.99.6] and CMP-sialic acid to give the sialylated product in 65 percent yield.

To illustrate the feasibility of the system for the synthesis of a soluble bioactive glycopeptide, the sialylated tripeptide released from the solid support by chymotrypsin-catalyzed hydrolysis (f) and was enzymatically fucosylated [E.C. 2.4.1.65] in step (g) to form sialyl Lewis X glycopeptide. The α1,3-fucosyltransferase-catalyzed reaction with GDP-fucose went to completion within 10 hours as monitored by HPLC. Because both Compounds 4a and 5a are substrates for the enzyme, the product mixture contained 35 percent of Compound 6, 20 percent of Compound 7 and 45 percent of the unreacted N-acetylglucosaminylated tripeptide, Compound 3b, respectively. To avoid the formation of 7, one can use α1,3-fucosyltransferase VII instead of fucosyltransferase V. See, Weston et al., *J. Biol. Chem.*, 267:4152–4160 (1992). Both enzymes are designated E.C. 2.4.1.65.

Scheme 3b

-continued
Scheme 3b

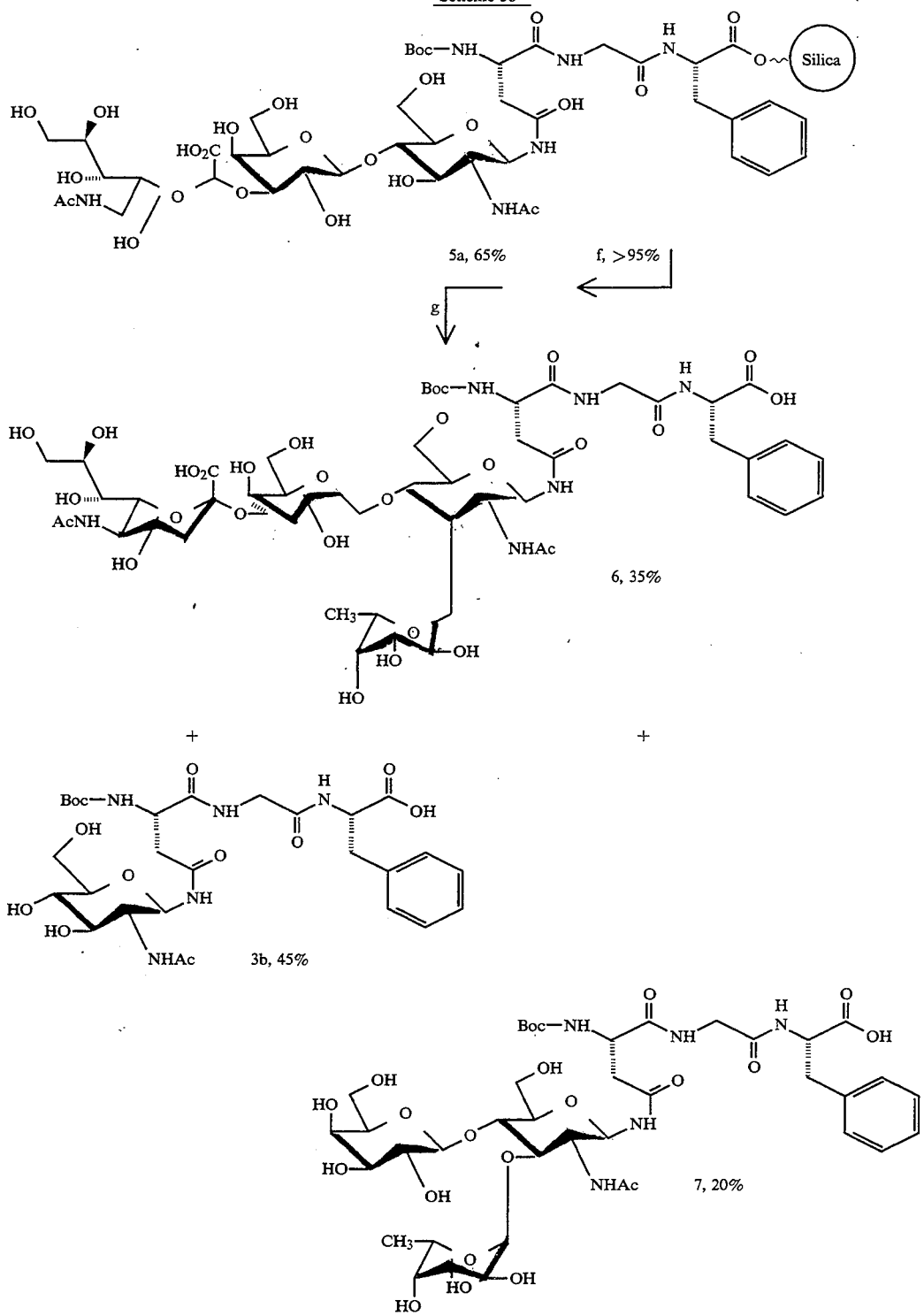

In summary, the solid phase system illustrated here supports both chemical peptide synthesis and glycosyltransferase-catalyzed sugar chain elongation and permits a rapid synthesis and controlled release of glycopeptides. The glycosylation reactions were performed in good yields. The system can also enable the synthesis of oligosaccharides as the peptide moiety can be removed enzymatically using endoglycosidases. [Trimble et al., Anal. Biochem., 141:522 (1984); Plummer, Biochemistry, 24:4665 (1985)]. In addition, glycopeptides displayed on the solid support can find use in the affinity purification of carbohydrate-binding proteins, the assay of binding and/or the catalysis of such proteins and the assembly of immobilized oligosaccharide libraries.

No effort was made here to optimize yields. Indeed, it is well known that the sugar nucleotide reactants used here are relatively unstable. As noted before, recycling systems that continually make further amounts of a desired sugar nucleotide can improve the yield of individual glycosyl coupling steps and thereby minimize deletion products.

Best Mode for Carrying out the Invention General

All solvents and reagents used were of the highest available purity. $^1$H-NMR was performed using a Bruker AMX-500 instrument. High-resolution mass spectra were recorded on a VG ZAB-ZSE under fast atom bombardment (FAB) conditions.

Peptide Synthesis

All reactions were carried out in capped 50 mL polyethylene centrifuge tubes. All reaction and washing steps were performed under shaking using a Maxi-Mix TM apparatus (Bearnstead/Thermolyne). Solvents were removed under reduced pressure after precipitation of the support. Usually, the support precipitated fast and completely. When this was not the case, the support was precipitated by centrifugation. The separated silica-based support was dried under a stream of dry nitrogen.

Monitoring of Enzymatic Reactions on Solid Phase

Aliquots of the reaction mixture containing 0.2–0.5 mg of silica-based support were washed with water and resuspended in 25 mL of 0.1M sodium phosphate (pH 7.0) containing α-chymotrypsin (Sigma, 1 mg/mL). The mixture was vortexed and shaken vigorously for five minutes. After centrifugation the supernatant was analyzed by HPLC.

HPLC

A DYNAMAX TM -60A semipreparative C8-reverse phase column (Rainin) was used for both analytical and preparative separations. Elution was performed by a gradient of methanol in 0.1 percent TFA (from 40 percent to 60 percent within 16 minutes) at a flow rate of 3 mL/min using a Gilson two pump high pressure mixing system equipped with a HOLOCHROM UV-detector (1=220 nm).

Abbreviations: GA, glycolic acid; APS, aminopropyl silica; TFA, trifluoroacetic acid; DIEA, diisopropylethylamine; BOP, benzotriazol-1-yloxytris(dimethylamino)phosphonium hexafluorophosphate; HOBt, 1-hydroxybenzotriazole.

EXAMPLE 1

Boc-Gly$_6$-APS, Structure 1

One gram of APS (aminopropyl silica gel, Sigma, 1.46 mmol/g), 145 mg (0.5 mmol) of Boc-Gyl$_3$-OH and 81.8 mg (0.6 mmol) HOBt were suspended in 5 mL DMF and 124 mg (0.6 mmol) of DCC was added under stirring. The pH was adjusted to 9.0 using DIEA (diisopropylethyl amine). After five hours, the support particles were separated by centrifugation and washed with 15 mL DMF and 15 mL CH$_2$Cl$_2$ (twice). Excess amino groups were capped using 2 mL pyridine/2 mL acetic anhydride in 20 mL CH$_2$Cl$_2$ overnight. The support was washed three times with CH$_2$Cl$_2$ (centrifugation) and N-deprotected in 25 percent TFA (in CH$_2$Cl$_2$) for two hours. The support was washed with CH$_2$Cl$_2$ (3×) and DMF (3×) and 1 mmol each Boc-Gly$_3$-OH (290 mg), HOBt (136 mg), DIEA (0.175 mL) and DCC (207 mg) were added under stirring. After twelve hours the completed support, Structure 1, (ninhydrin-negative) was washed thoroughly (15 mL DMF 3×, 15 mL CH$_2$Cl$_2$ 3×).

EXAMPLE 2

Boc-Phe-GA-Gly$_6$-APS, Structure 2

After N-deprotection of 1 as described above, 1 g of support was shaken in the presence of 485 mg (1.5 mmol) Boc-Phe-GA-OH, 202 mg (1.5 mmol) HOBt, 0.66 g (1.5 mmol) BOP and 0.483 mL (2.75 mmol) DIEA until the coupling was complete. An aliquot of the washed and dried reacted support was subjected to chymotrypsin hydrolysis (0.1M phosphate buffer, pH 7.0) and analyzed by HPLC. Based on HPLC results, the substitution level was estimated to be 0.2 mmol/g.

EXAMPLE 3

Boc-Asn(GlcNAc$\beta$)-Gly-Phe-GA-Gly$_6$-APS, Structure 3a

After deprotection (25 percent TFA), washing and drying, 0.9 g of support-linked 2 was shaken in the presence of 262 mg (1.5 mmol) Boc-Gly-OH, 665 mg (1.5 mmol) BOP, 203 mg HOBt and 0.27 mL (1.5 mmol) DIEA until the reaction was complete. The N-Boc group was removed, and 220 mg (0.5 mmol) of Boc-Asn($\beta$GlcNAc)-OH, 222 mg (0.5 mmol) of BOP and 0.0158 mL (0.9 mmol) of DIEA were added to 0.5 g (about 0.1 mmol) of the deprotected support in 5 mL DMF and shaken for one hour. Both completion and selectivity of coupling were verified by HPLC analysis after chymotryptic cleavage.

EXAMPLE 4

Boc-Asn(GlcNAc$\beta$)-Gly-Phe-OH; Compound 3b

Forty milligrams of support-linked 3a were subjected to α-chymotrypsin-catalyzed hydrolysis. The soluble product (5.0 mg, 7.8 mmol; resulting substitution level: 0.2 mmol/g support) was purified by RP-HPLC and characterized: $^1$H NMR (500 MHz, D$_2$O) δ1.24 (s, 9H, Boc), 1.79 (s, 3H, NAc), 2.50–2.61 (m, 2H, C$_\beta$-H$_2$ of Asn), 2.82 (dd, 1H, J=9.5, 14.0 Hz, C$_\beta$-H of Phe), 3.09 (dd, 1H, J=5.0, 14.0 Hz, C$_\beta$-H of Phe), 3.28–3.32 (m, 2H), 3.41 (t, 1H, J=8.7 Hz), 3.56 (dd, 1H, J=4.0, 12.0 Hz), 3.58–3.73 (m, 4H), 4.24 (dd, 1H, J=5.5, 7.0 Hz, C$_\alpha$-H of Asn), 4.51 (dd, 1H, J=5.0 9.5 Hz, C$_\alpha$-H of Phe), 4.87 (d, J=9.5 Hz, H-1 of GlcNAc), 7.03–7.20 (m, 5H, C$_6$H$_5$ of Phe); FAB+−MS calcd. for C$_{28}$H$_{41}$N$_5$O$_{12}$+H+ 640.2830, found 640.2850; calcd. for C$_{28}$H$_{41}$N$_5$O$_{12}$+Na+ 662, found 662; calcd. for C$_{28}$H$_{41}$N$_5$O$_{12}$-H++2Na+ 684, found 684.

EXAMPLE 5

β1,4-Galactosylation

Sixty milligrams (0.012 mmol) of support-linked 3a were suspended in 1 mL water. After addition of 3 mg of BSA, the suspension was shaken for five minutes and washed 5× with 0.1M HEPES (pH 7). The precipitate was suspended in 0.7 mL of the same buffer and 7 mL of 1M MnCl$_2$, 9.5 mg (12 mmol) of UDP-Gal and 2U of bovine β1,4galactosyltransferase (E.C. 2.4.1.22; Sigma) were added. The mixture was shaken at 300 rpm and the reaction was monitored by HPLC. After five hours, 5 U of alkaline phosphatase (Pharmacia) were added. The reaction was stopped after 10 hours. α-Chymotrypsin hydrolysis and analysis indicated that 55 percent of support-linked 3a was converted to support-linked 4a.

EXAMPLE 6

Boc-Asn (Galβ1,4GlcNAcβ)-Gly-Phe-OH, Compound 4b

Following the galactosylation reaction, 20 mg of the glycosylpeptide-support were subjected to α-chymotrypsin-catalyzed hydrolysis. The galactosylated glycopeptide fraction Compound 4b (1.7 mg) was separated by RP-HPLC and characterized: $^1$H NMR (500 MHz, $D_2O$) δ1.25 (s, 9H, Boc), 1.79 (s, 3H, NAc), 2.57 (m, 2H, $C_\beta$-H$_2$ of Asn), 2.82 (dd, 1H, J=9.5, 14.7 Hz, $C_\beta$-H of Phe), 3.09 (dd, 1H, J=5.5, 14.7 Hz, $C_\beta$-H of Phe), 3.36 (dd, 1H, J=8.0, 9.7 Hz), 3.45 (m, 1H), 3.48 (dd, 1H, 3.3, 9.9 Hz), 3.52-3.61 (m, 5H), 3.61-3.71 (m, 2-3H), 3.73 (m, 2H), 4.24 (m, 1H, Ca-H of Asn), 4.29 (s, 1H, J=8.0 Hz, H-1 of Gal), 4.51 (dd, 1H, J=5.0, 9.5 Hz, $C_\alpha$-H of Phe), 4.90 (d, 1H, J=9.5 Hz, H-1 of GlcNAc), 7.03-7.23 (m, 5H, $C_6H_5$ of Phe); FAB+ —MS calcd. for $C_{34}H_{51}N_5O_{17}$+Na+ 824.3178, found 824. 3180; calcd. for $C_{34}H_{51}55O_{17}$+H+ 802, found 802: calcd. for $C_{34}H_{51}N_5O_{17}$-H++2Na+ 846, found 846.

EXAMPLE 7

α2,3-Sialylation, Structure 5a

One hundred milligrams of support-linked galactosylation product, 4a, and 10 mg (0.015 mmol) of CMP-NeuAc were suspended in 1 mL of 0.1M HEPES (0.1M, pH 7.0) containing 5 mM $MnCl_2$. α2,3Sialyltransferase (E.C. 2.4.99.6; 0.1 mL, Cytel) was added and the mixture was shaken for 34 hours. The solid phase was separated, washed and dried. A sample of the resulting solid phase was subjected to chymotryptic cleavage. RP-HPLC of the supernatant indicated that 65 percent of support-linked 4a was converted to support-linked 5a. Accordingly, the solid phase contained about 36 percent of support-linked 5a after this step.

EXAMPLE 8

Boc-Asn (NeuAcα2,3Galβ1,4GlcNAcβ)-Gly-Phe-OH, Compound 5b

Thirty milligrams of the solid support-linked 5a were subjected to chymotryptic hydrolysis, and Compound 5b (2.1 mg) was isolated by HPLC and characterized: $^1$H NMR (500 MHz, $D_{20}$) δ1.30 (s, 9H, Boc), 1.68 (t, 1H, J=12.2 Hz, H-3ax of NeuAc), 1.83 (s, 3H, NAc of GlcNAc), 1.90 (s, 3H, NAc of NeuAc), 2.60-2.65 (m, 3H, H-3eq of NeuAc, $C_\beta$-H$_2$ of Asn), 2.86 (dd, 1H J=9.1, 13.8 Hz, $C_\beta$-H of Phe), 3.14 (dd, 1H, J=4.5, 13.8 Hz, $C_\beta$-H of Phe), 3.4-3.83 (m, 20H), 3.99 (dd, 1H, J=3.0, 10.0 Hz,), 4.29 (dd, 1H, J=5.5, 7.0 Hz, $C_\alpha$-H of Asn), 4.42 (d, 1H, J=8.0 Hz, H-1 of Gal), 4.53 (dd, 1H J=5.0, 9.5 Hz, $C_\alpha$-H of Phe), 4.94 (d, 1H, J=9.5 Hz, H-1 of GlcNAc), 7.09-7.26 (m, 5H, $C_6H_5$ of Phe); FAB+—MS calcd. for $C_{45}H_{68}N_6O_{25}$+Na+ 1115.44132, found 1115.4125; calcd. for $C_{45}H_{68}N_6O_{25}$-H++2Na+ 1137, found 1137; calcd. for $C_{45}H_{68}N_6O_{25}$-2H++3Na+ 1159, found 1159.

EXAMPLE 9

α1,3-Fucosylation

Fifty milligrams of sialylated solid phase were suspended in 0.2 mL of water and shaken in the presence of α-chymotrypsin (Sigma, 2 mg/mL) at pH 7.0 for one hour. The mixture was ultrafiltered and washed with 0.2 mL of water. The filtrate was concentrated in vacuo using a SpeedVac ™ Concentrator (SAVANT). α1,3-Fucosyltransferase V (E.C. 2.4.1.65; 0.1 mL, Cytel) was lyophilized and redissolved in 0.5 mL 0.1M HEPES (pH 7.3) containing 5 mM ATP, 20 mM $MnCl_2$. This solution was added to the substrate concentrate and the reaction was started by addition of 5 mg (8 mmol) of GDP-Fuc. The reaction was followed by HPLC. After 10 hours, both Compounds 4b and 5b were completely fucosylated. The two fucosylation products (Compounds 6 and 7) were isolated and characterized by RP-HPLC.

A. Boc-Asn (NeuAcα2,3Galβ1,4GlcNAcβ(Fucα1,3))-Gly-Phe-OH, Compound 6

Isolated: 2.5 mg; $^1$H NMR (500 MHz, $D_2O$) δ1.03 (d, 3H, J=6.5 Hz, 6-$CH_3$ of Fuc), 2.29 (s, 9H, Boc), 1.672 (t, 1H, J=12.0 Hz, H-3ax of NeuAc), 1.83 (s, 3H, NAc of GlcNAc), 1.89 (s, 3H, NAc of NeuAc), 2.55-2.65 (m, 3H, H-3eq of NeuAc and $C_\beta$-H$_2$ of Asn), 2.87 (dd, 1H, J=9.3, 14.0 Hz, $C_\beta$-H of Phe), 3.14 (dd, 1H, J=4.5, 14.0 Hz, Cb-H of Phe), 3.40 (dd, 1H, J=7.8, 9.8 Hz), 3.42-3.86 (m, 24 H), 3.95 (dd, 1H, J=2.8, 9.9 Hz), 4.28 (m, 1H, $C_\alpha$-H of Asn), 4.40 (d, 1H, J=7.5 Hz, H-1 of Gal), 4.54 (dd, 1H, J=5.0, 8.8 Hz, $C_\alpha$-H of Phe), 4.95 (d, 1H, J=4.0 Hz, H-1 of Fuc), 4.98 (d, 1H, J=10.0 Hz, H-1 of GlcNAc), 7.09-7.25 (m, 5H, $C_6H_5$ of Phe); MS (Ion-spray ionization mode): calcd. for $C_{51}H_{78}N_6O_{29}$-H+ 1237.5, found 1238; calcd. for $C_{51}H_{78}N_6O_{29}$-2H++Na+ 1260, found 1260.

B. Boc-Asn [Galβ1,4(Fucα1,3)GlcNAcβ]-Gly-Phe-OH, Compound 7

Isolated: 1.0 mg; $^1$H NMR (500 MHz, $D_2O$) δ1.11 (d, 3H, J=6.5 Hz, 6-$CH_3$ of Fuc), 1.36 (s, 9H, Boc), 1.89 (s, 3H, NAc of GlcNAc), 2.65 (m, 2H, $C_\beta$-H of Phe), 2.87 (m, 1H, $C_\beta$-H of Phe), 3.16 (m, 1H, $C_\beta$-H of Phe), 3.44 (dd, 1H, J=8.0, 9.5 Hz), 3.50-3.93 (m, 18H), 4.36 (m, 1H, $C_\alpha$-H of Asn), 4.41 (d, 1H, J=8.0 Hz, H-1 of Gal), 4.45 (m, 1H, $C_\alpha$-H of Phe), 5.04 (d, 1H, J=3.5 Hz, H-1 of Fuc), 5.08 (d, 1H, J=10.0 Hz, H-1 of GlcNAc), 7.13-7.31 (m, 5H, $C_6H_5$ of Phe); FAB+ —MS calcd. for $C_{40}H_{61}N_5O_{21}$+Na+ 970.3757, found 970.3745; calcd. for $C_{40}H_{61}N_5O_{21}$-H++2Na+ 992, found 992.

Although the present invention has been described in some detail by way of illustration and example for purposes of clarity and understanding, certain obvious modifications can be practiced with the scope of the appended claims.

We claim:

1. A process for the in vitro synthesis of a glycopeptide that comprises the steps of:
   (a) providing a particulate solid matrix comprising a silica-based solid support having a plurality of two-part spacer groups covalently linked to the surface of the particles, said spacer groups having a proximal end and a distal end and a chain length equal to that of about 12 to about 40 methylene groups, said proximal end including the first part of the spacer and providing said covalent link to the particles, said distal end including the second part of the spacer and having a terminal amine or hydroxyl group, the first spacer part having a length equal to that of 3 to about 10 methylene groups and being covalently linked to the second spacer part, said second spacer part having a length equal to that of about 9 to about 30 methylene groups, said second spacer part being soluble as a free molecule in water, dimethylformamide and dichloromethane;

(b) coupling the α-carboxyl group of zero to about five amino acid residues to said terminal amine or hydroxyl group of the spacer group to provide a terminal free amine;

(c) coupling a moiety having a selectively severable bond to the free amino or hydroxyl group (i) of said solid matrix when zero residues are added in step (b) or (ii) of an α-amino group of an amino acid residue coupled in step (b) to form a selectively severable matrix, said selectively severable moiety also including an amino or hydroxyl group breaking of said selectively severable bond freeing the solid matrix from anything bonded to the moiety having the selectively severable bond;

(d) coupling the α-carboxyl group of zero to about five amino acid residues to the amino or hydroxyl group of the selectively severable matrix to provide an amino group;

(e) coupling the α-carboxyl group of a glycosyl amino acid or glycosyl peptide containing up to about five amino acid residues to the amino or hydroxyl group (i) of the selectively severable matrix when zero residues are coupled in step (d) or (ii) of an α-amino group of an amino acid residue coupled in step (d) to form a glycosyl peptide;

(f) enzymatically coupling a further glycosyl moiety to the formed glycosyl peptide in an aqueous medium to form an oligoglycosyl peptide;

(g) repeating step (f) zero to about five times with the same or different glycosyl moiety and enzyme; and (h) selectively severing said selectively severable bond to free the oligoglycosyl peptide from said solid matrix.

2. The process according to claim 1 wherein said first spacer part is a $C_2$–$C_6$ alkylene-ω-amine whose ω-amine is covalently linked to said second spacer part.

3. The process according to claim 1 wherein said second spacer part has a length equal to that of about 12 to about 24 methylene groups.

4. The process according to claim 1 wherein zero amino acid residues are added in step (b).

5. The process according to claim 1 wherein said selectively severable bond is enzymatically severable in an aqueous medium.

6. The process according to claim 1 wherein each coupling step prior to step (f) is carried out under substantially anhydrous conditions.

7. The process according to claim 1 including the further step (g) of recovering the freed oligoglycosyl peptide.

8. The process according to claim 1 wherein said glycosyl peptide is coupled enzymatically as a di- or longer peptide having a carboxy-terminal $C_1$–$C_6$ ester, said glycosyl group being bonded to other than the carboxy-terminal amino acid residue.

9. The process according to claim 1 wherein the amino group of said solid matrix is the α-amine of a $C_2$–$C_3$ amino acid residue.

10. A process for the in vitro synthesis of a glycopeptide that comprises the steps of:

(a) providing a particulate solid matrix that comprises a silica-based solid support having a plurality of two-part spacer groups covalently linked to the surface of the particles, said spacer groups having a proximal end and a distal end and a chain length equal to that of about 15 to about 30 methylene groups, said proximal end including the first part of the spacer and providing the covalent link to the particles, said distal end including the second part of the spacer and having a terminal amine or hydroxyl group, the first spacer part being an ω-amino-$C_2$–$C_6$ alkylene group whose ω-amine is covalently linked to said second spacer part; said second spacer part having a length equal to that of about 12 to about 24 methylene groups, said second spacer part being soluble in water, dimethylformamide and dichloromethane;

(b) coupling the α-carboxyl group of zero to about five amino acid residues to said amine or hydroxyl group under substantially anhydrous reaction conditions to provide a terminal free amine;

(c) coupling under substantially anhydrous conditions a moiety having a selectively severable bond to the amino or hydroxyl group (i) of said solid matrix when zero residues are added in step (b) or (ii) of an α-amino group of an amino acid residue coupled in step (b) to form a selectively severable matrix, said selectively severable moiety also including an amino group, the breaking of said selectively severable bond freeing the solid matrix from anything bonded to the moiety having the selectively severable bond;

(d) coupling under substantially anhydrous conditions the α-carboxyl group of zero to about five amino acid residues to the amino or hydroxyl group of the selectively severable matrix to provide an amino group;

(e) coupling under substantially anhydrous conditions the α-carboxyl group of a glycosyl amino acid or glycosyl peptide containing up to about five amino acid residues to the amino or hydroxyl group (i) of the selectively severable matrix when zero residues are coupled in step (d) or (ii) of an α-amino group of an amino acid residue coupled in step (d) to form a glycosyl peptide;

(f) enzymatically coupling a further glycosyl moiety to the formed glycosyl peptide in an aqueous medium to form an oligoglycosyl peptide;

(g) repeating step (f) zero to about five times using a different glycosyl moiety and enzyme for each repeat;

(h) selectively severing said selectively severable bond to free the oligoglycosyl peptide from said solid matrix; and (i) recovering the freed oligoglycosyl peptide.

11. The process according to claim 10 wherein said second spacer part is an oligo-$C_2$–$C_3$-peptide or amine-terminated oligo-$C_2$–$C_3$-alkylene oxide.

12. The process according to claim 10 wherein said severable bond is enzymatically severable in an aqueous medium.

13. The process according to claim 10 wherein the glycosyl group of the amino acid or peptide coupled in step (e) is linked to the oxygen of a serine or threonine residue side chain or to the amido nitrogen of an asparigine or glutamine side chain.

* * * * *